MINT STRAIN
Filed Sept. 15, 1967
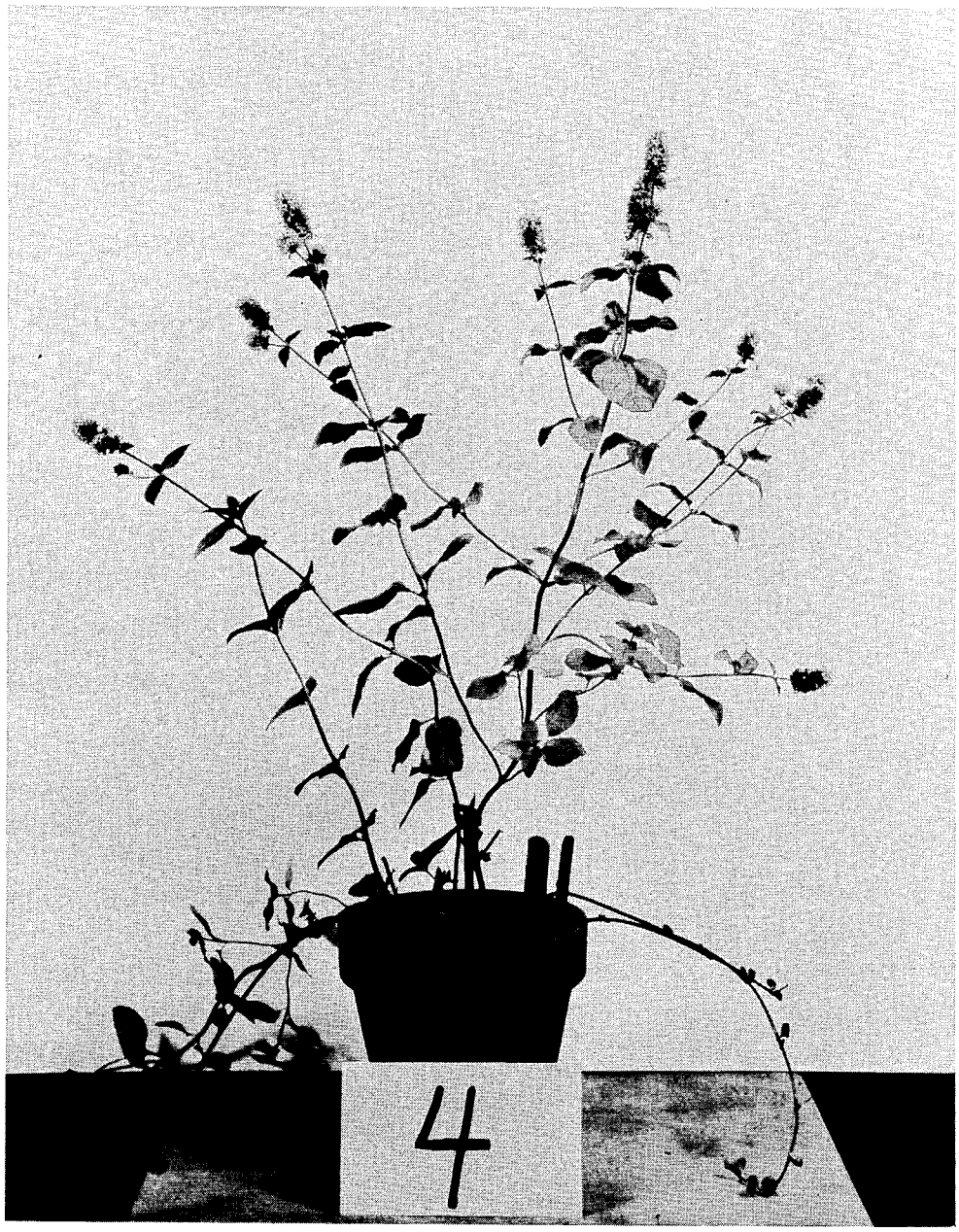

MINT STRAIN
Filed Sept. 15, 1967
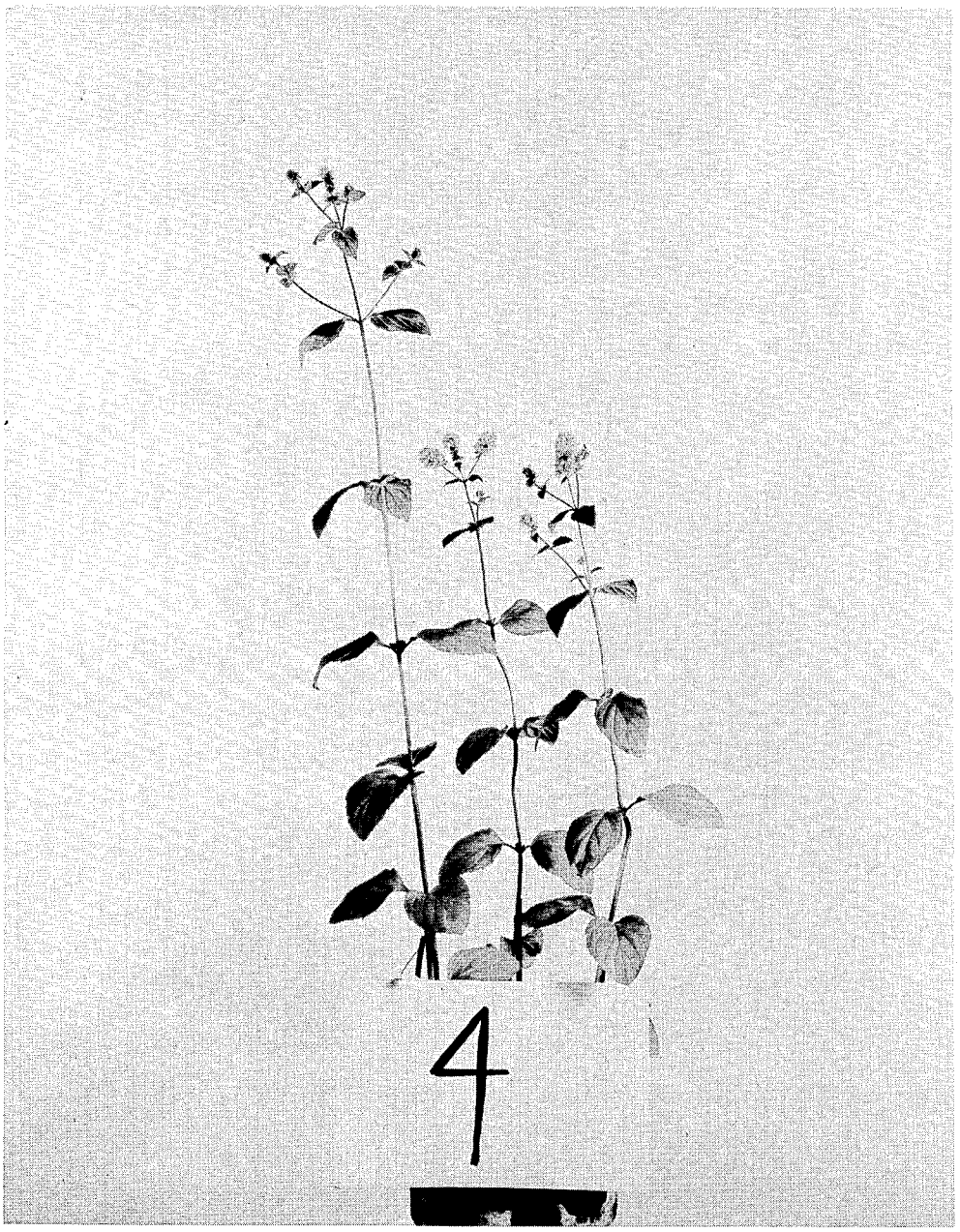

United States Patent Office

Plant Pat. 2,907
Patented July 22, 1969

2,907
MINT STRAIN

Merritt J. Murray, Kalamazoo, Mich., assignor to A. M. Todd Company, Kalamazoo, Mich., a corporation of Michigan Filed Sept. 15, 1967, Ser. No. 668,259
Int. Cl. A01h 5/00
U.S. Cl. Plt.—89 1 Claim

ABSTRACT OF THE DISCLOSURE

A new and distinct variety of mint plant substantially as herein shown and described, being an adapted high-yielding strain characterized particularly by its production of an oil with a relatively high linalyl acetate content, when compared to the oil of its *Mentha citrata* seed parent, and at most only minor amounts of menthone and pulegone, which are the principal components of the oil of its male parent, said oil having a pleasant lavender odor with definite terpeneless bergamot characteristics; its excellent stolons which are winter hardy; and its hardy characteristics under climatic conditions favorable to the growth of mint plants as represented by *Mentha piperita* L., especially in the Oregon and Idaho areas of mint production.

This invention relates to a new and distinct variety of mint plant which was originally produced by hybridizing a clonal strain (European origin unknown) of diploid *Mentha citrata* Ehrh. as a seed parent to a pollen parent which was a highly Verticillium wilt-resistant selection known as 59–198. The male parent, 59–198, was a specific wilt-resistant selection from a sib cross of two highly wilt-resistant $S_1$ inbreds (or once self-pollinated first generation inbreds) of *Mentha crispa* L. (also taxonomically known as *Mentha spicata* L. var. *crispata*).

Drawings

In the drawings, which are photographic illustrations of the new variety, the figures (2) are both views of the plant showing the general form of the stems, leaves, and flowers.

Seed parent

In the above cross, the Mueller strain of *Mentha citrata* had to be the seed parent since it is male sterile.

Male parent

The male parent used in the cross was known in our laboratory as 59–198 when it was hybridized, but it was actually derived from a sib cross made in 1950 and the seedlings were grown in 1951 as Culture 51–1226. The selected seedling from Culture 51–1226 known as number 1 had no rust, no Verticillium wilt symptoms, and a weak menthone odor. It had very slightly hairy stems, a very erect habit, and early maturity (medium maturity for *M. crispa* lines, but early maturing in comparison to seed parent and hybrids) with small crisp leaves. This selection should have had and did have high wilt resistance since it came from the cross of two selected first generation $S_1$ inbreds of *M. crispa* which had been selected for their superior wilt resistance in 1948. To recapitulate the history of the $S_1$ inbreds, we self-pollinated a clonal strain of *Mentha crispa* L. in the summer of 1947 and planted the selfed seeds in the spring of 1948 as Cultures 48–202 and 48–201. We selected two seedlings as being very superior in Verticillium wilt resistance and these were very thoroughly tested in 1949 and designated a 202–3 and 201–9. As we have noted previously, these two first generation inbreds were hybridized, or sib-crossed, in the summer of 1950 to give Culture 51–1226 from which we selected the single seedling that was used as a male parent and known in our laboratory as 59–198. The disease resistance and vigor of this wilt-resistant selection (59–198) were confirmed through subsequent field tests made during the nine-year period between its initial selection in 1951 and its utilization in 1961 in the hybridization to *Mentha citrata*.

As one can note, the Plot 4 strain was derived from the interspecific hybridization of two species, *Mentha citrata* Ehrh. and *Mentha crispa* L. The Mueller strain of *Mentha citrata* was utilized in this program and its European origin is unknown to us. *Mentha crispa* was a clonal strain from the original A. M. Todd collection of species from European sources made a considerable number of years ago and its exact geographical origin is unknown.

History and first vegetative propagation

The hybridization of the Mueller strain of *Mentha citrata* and 59–198 was accomplished in the summer of 1961. About seven hundred seeds were planted in the spring of 1962 as Culture 62–1006. We transplanted 677 seedlings and 325 of these from this specific cross were grown on the Mueller farm as numbers 4830 to 4981 and 6710 to 6882. Of these 325 seedlings, 233 were discarded at harvest time, whereas 92 were assigned to harvest numbers 1412 to 1469 and 1889 to 1922. The single plant harvested as 62–1421 gave on distillation 4.95 grams of oil which was odor evaluated and assayed by vapor chromatography.

This strain was first vegetatively propagated in April 1963 to give a six-foot plot numbered 63–246. Its oil quality, yield and disease resistance were studied in this 1963 six-foot plot and subsequently in a $\frac{1}{100}$ acre plot in 1964, known as Plot 64–88. This strain was further tested in 1965 in a $\frac{1}{20}$ acre plot known as 1965 Plot 4. We have further propagated this strain in a greenhouse in Caldwell, Idaho during the winter of 1965–66 and five acres were grown in Idaho in the summer of 1966. The wilt-resistance test of the Plot 4 strain was conducted in Indiana during the summers of 1965, 1966 and 1967.

General objectives of this breeding program

The specific cross giving rise to Plot 4 was made for the following reasons. We utilized the Mueller strain of *Mentha citrata*, since it is our tallest strain of *Mentha citrata*. We chose 59–198 as the male parent since we wished to hybridize to a very highly wilt-resistant male parent so that our resulting hybrids might have a considerable degree of wilt resistance. This was deemed important since all our stock strains of *Mentha citrata* are extremely susceptible to Verticillium wilt. Any hybrid to be usable must also be better adapted to the climatic conditions of the U.S. mint-growing areas than our native European stock strains of *Mentha citrata* appear to be. A suitable hybrid must also have excellent stolons and over-winter better than any of the natural strains of *Mentha citrata* which we have tested.

Distinctive characteristics of Plot 4

While one could say that this Plot 4 strain is intermediate in appearance between the parental strains, it is readily distinguishable from either of the parents in the following ways.

Difference between *Mentha citrata* and Plot 4

*Height.*—The Plot 4 strain is slightly taller than the seed parent and the Plot 13 hybrid strain and is much taller than the male parent. On the alluvial soil of the Oregon production area, the seed parent strain of *Mentha citrata* Ehrh. was 17–20″ tall while the Plot 4 strain was 17–26″ tall in its first year growth and was generally 25–26″ tall in the second year growth. On the alluvial soil of the Idaho production area, the Plot 4 hybrid was 18–26″ tall. Contrariwise, under greenhouse conditions the Plot 4 strain was 38–46″ tall and shorter than the seed parent which was 58–72″ tall. The upper limits given in the field height measurements are those obtained under near-optimum conditions.

*Plant habit.*—The Mueller strain of *Mentha citrata* has an erect, bush type plant habit with few branches rising mostly in the upper half of the plant and having an open habit with large, nearly flat leaves. The Plot 4 hybrid strain is somewhat similar to the seed parent in plant habit, since it also has a tall, somewhat late-maturing, bush type habit which is spreading and open with coarse stems and large flat leaves that do not make a very dense foliage, but the Plot 4 hybrid is more branched with a more spreading bush type habit having denser foliage than that characteristic of the seed parent. At maturity, the plant tops of tall field plants may lop in the Plot 4 strain whereas this seldom occurs in the seed parent strain. The seed parent strain of *M. citrata* Ehrh. does not have a reclining or sprawling habit as do many other strains of *M. citrata* Ehrh.

*Maturity.*—The Plot 4 strain has medium plus maturity with both the first and second year herbage in full bloom on September 1st, whereas the seed parent has very late maturity with very few flower spikes in bloom on September 1st.

*Yield.*—The Plot 4 strain yields 70–78 lbs. of oil per acre, whereas the seed parent generally does not yield more than 30 or 40 lbs. of oil per acre, and at best never has yielded more than 50 lbs. per acre under our test conditions.

*Stems.*—The seed parent strain of *Mentha citrata* has coarse, large stems which are brittle and tend to split rather than lop or recline. The Plot 4 hybride has medium-sized, very sturdy, erect, somewhat branched stems which are less coarse and definitely much less brittle than those of the seed parent. The stem of the Plot 4 strain generally remain erect at maturity or lop slightly at the top. (The stems of the Plot 4 strain are often coarser and definitely much less branched than those of the Plot 13 strain hybrid.)

*Degree of stem branching.*—The seed parent has relatively few secondary branches and almost no tertiary branches, whereas the Plot 4 hybrid strain is more branched with numerous secondary branches and a few tertiary branches. (While the Plot 4 strain has a few tertiary branches, it is much less branched than the Plot 13 hybrid strain which has numerous tertiary branches and is very freely branched.)

*Stem size.*—The stem diameter of the seed parent is usually 4–5 mm., while the stems of the Plot 4 hybrid are less coarse and usually 2.75–3 mm. in diameter. Under greenhouse conditions, the seed parent has stems which are 3–5 mm. in diameter, whereas the Plot 4 strain has stems which are 3–3.5 mm. in diameter.

*Leaf shape.*—Strains of *Mentha citrata* frequently have oval to ovate leaves but the seed parent strain used in our breeding program has ovate leaves. The Plot 4 strain typically has ovate leaves which are frequently narrowly ovate, with the uppermost leaves sometimes aproaching an ovate-lanceolate shape since they taper to an acute apex. Leaf shape is not a prime distinguishing characteristic between the seed parent and the Plot 4 strain but does distinguish both from many other strains of *Mentha citrata* which have oval-shaped leaves with cordate or subcordate leaf bases.

*Leaf size.*—The lower mainstem leaves of the Plot 4 strain measure 1½–2⅝″ long x 1–1¼″ wide, but the upper leaves are generally smaller and measure ⅞–1½″ long. In the greenhouse, the mainstem leaves of the Plot 4 strain are sometimes 3″ long x 2″ wide, whereas those of the Mueller strain of *Mentha citrata* under similar conditions are 2⅞″ long x 1 11/16″ wide, and those of the Todd strain of *Mentha citrata* 1–1½″ long x 1¼″ wide. In short, the Plot 4 strain usually has slightly larger leaves than the Mueller strain of *Mentha citrata* (especially in first-year plants) and definitely has much larger leaves than the Plot 13 strain. In fact, the Plot 4 strain has larger leaves than any of the parental strains of *Mentha citrata* that I have observed with the exception of the Thomas strain of *Mentha citrata.*

*Leaf petiole.*—The leaf petioles of the greenhouse-grown plants of the seed parent are usually 15–20 mm. long, whereas those of the Plot 4 strain are usually 11–15 mm. long in the mature mainstem leaves of greenhouse grown plants. Field plants of the Plot 4 strain grown in Idaho or Oregon usually have leaf petioles which are 8–13 mm. long but infrequently only 6 mm. long. In summary, the Plot 4 strain has shorter petioles than the seed parent but longer petioles than the Plot 13 hybrid and definitely longer than the leaf petioles of the male parent (which has nearly sessile leaves).

*Leaf apex.*—While some *Mentha citrata* strains have rounded or very obtuse leaf apexes, the seed parent strain has an acute leaf apex and is similar to the Plot 4 hybrid. The lower mainstem leaves of greenhouse-grown plants of the Plot 4 strain sometimes have rounded or obtuse leaf apexes but the upper, smaller leaves definitely have acute leaf apexes.

*Leaf base.*—The mainstem leaves of both the seed parent strain of *Mentha citrata* and the Plot 4 strain are rounded to an acute point on the leaf petiole and are definitely not cordate or subcordate and both sides are usually similar or equal. Juvenile leaves of the stolon sprouts and a few of the lowest mainstem leaves of the Plot 4 strain occasionally have cordate bases, but typical leaves of both the seed parent and the Plot 4 strain have acute leaf bases, and thus differ from many other strains of *Mentha citrata* which have cordate leaf bases. The leaf base of the seed parent strain generally forms a more acute angle with the leaf petiole (λ versus λ) than does Plot 4 (λ).

*Leaf margin.*—While some strains of *Mentha citrata* have very inconspicuous teeth on the leaf margin, the seed parent strain of *Mentha citrata* has regular, serrate, very conspicuous teeth. The Plot 4 strain is similar in having regular, serrate, conspicuous teeth which are slightly less prominent than those of the seed parent strain.

*Leaf teeth.*—The teeth of both the seed parent strain of *Mentha citrata* and those of the Plot 4 strain measure 1.5 mm. on the sharp edge where best developed. The reason the teeth of the seed parent appear more conspicuous than those of Plot 4 seems to be due to the more acute shape of the tooth in the Mueller strain (λ vs. λ) and to the fact that the teeth protrude more distinctly from the leaf blade. In both strains there are about 12 or 13 teeth on a leaf side.

*Leaf texture.*—While certain strains of *Mentha citrata* have definitely coriaceous, or leathery, leaf texture, the seed parent and the Plot 4 strain are alike in having a normal, non-coriaceous leaf texture.

*Leaf color.*—The leaves of the Plot 4 strain have a normal green color, whereas the leaves of the seed parent under certain environmental conditions may develop some anthocyanin coloration and have a bronzed appearance. This characteristic is somewhat variable since the anthocyanin color requires sunlight for development.

*Leaf contour.*—In the seed parent strain of *Mentha* citrata, leaf tips of the mature leaves of the main axis curl or roll downward, often making a half circle, whereas the mature leaves of the Plot 4 strain tend to project flat, or extend flat, with the leaf tip very little turned downward.

*Leaf surface.*—While the leaves of all *Mentha citrata* strains are flat, they do have very prominent veins and often may have considerable wrinkling upward of the leaf tissue between the major veins, especially in greenhouse-grown plants. The leaves of the Plot 4 strain are flat and are *not* wrinkled between the major veins.

*Flower spikes.*—The flower spikes of the seed parent are typically capitate, or dome-shaped, as in *Mentha aquatica* L., whereas the Plot 4 strain hybrid has an elongate, narrowly cylindrical flower spike, which is frequently blunt or obtuse on both ends at maturity and having the flower clusters crowded to make a dense, compact spike. The terminal cylindrical flower spikes of the Plot 4 strain are quite peppermint-like as opposed to the capitate, or globose flower spikes of *Mentha citrata* and *Mentha aquatica* L. While the male parent also has a cylindrical spike, the spike of the male parent is very slender and resembles the flower spike of *Mentha crispa* from which it was derived. In comparison to the Plot 13 hybrid, the Plot 4 flower spikes are more crowded and the flower spikes are broader and larger in Plot 4.

*Flower spike size.*—The capitate heads of the seed parent are ½–¾" long x ½–¾" wide with the dome-shaped heads usually as wide as long, whereas the end portion of the terminal flower spikes of the hybrid are usually 1⅜" long x ½" wide. The terminal capitate heads of the seed parent in metric measurements are 13–20 mm. long x 13–20 mm. wide, about as wide as long, whereas the complete terminal spikes of the Plot 4 hybrid are usually 30–50 mm. long (end portion typically 30–35 mm. long) x 12–16 mm. wide with the second year herbage having smaller, more numerous flower spikes measuring 20–22 mm. long x 10–12 mm. wide. While the fruiting heads of the male parent strain may be 20–40 mm. long, occasionally even 50 mm., the fruiting spikes are only 6–7 mm. broad, whereas those of the Plot 4 hybrid are generally 10–14 mm. broad and those of the Plot 13 hybrid 7–9 mm. broad.

*Corolla color.*—While the seed parent and the Plot 13 hybrid have a medium lavender flower color, the Plot 4 strain has a dark lavender flower color under field conditions. This is not true in greenhouse plants since the flowers of the Plot 4 strain are lighter than either the seed parent or the Plot 13 hybrid. (Disregard corolla color as a distinguishing characteristic since it is influenced by environmental factors.)

*Flower spike subtended by.*—The flower spikes of all *M. citrata* strains are terminal with only one or two subaxillary clusters at the base and are usually subtended by half-size to full-size leaves depending upon the strain, but the terminal flower spikes of the seed parent and of the Plot 4 strain are subtended by very small leaves which are no more than 1/10 to ¼ the size of the mainstem leaves. While the Plot 4 strain and the seed parent have about the same bract size, the bracts of the Plot 4 strain are usually more slender with a lanceolate shape, whereas those of the seed parent are broader and ovate.

*Extent of flowering.*—The seed parent produces small flower heads sparingly by September 1st, whereas the Plot 4 hybrid strain produces a profusion of large flower spikes under field conditions, especially in the second year herbage.

*Stolons.*—While the seed parent strain of *Mentha citrata* has very long and slender stolons in greenhouse-grown plants, stolon production in the field in the western mint-growing areas is erratic and is frequently inadequate to maintain the strain well. In contrast, the Plot 4 strain has excellent stolons which are similar to those of peppermint.

*Stolon survival.*—Since the seed parent strain of *M. citrata* when grown in western mint areas sometimes has only crowns, or 1–2" long stolons, survival over winter is erratic and uncertain and often inadequate to maintain an agricultural stand. In contrast, the Plot 4 strain has excellent stolons which have the unique property of overwintering well (from all present evidence), thus resembling its male parent.

*Oil composition.*—On the basis of a three-year average, the seed parent had 58% linalyl acetate, 30% linalool and 12% other components, whereas the hybrid has 73% linalyl acetate, 17% linalool and 10% other. The Plot 4 strain has a much higher linalyl acetate content and a lower linalool content than the seed parent. We do not presume that the minor oil constituents of a terpene hydrocarbon nature are identical to those in the seed parent.

*Odor.*—The seed parent has a typical *Mentha citrata* odor, whereas the Plot 4 strain has been said to have a terpeneless bergamot-like odor with minty by-notes minimum or absent.

*Stem or plant color.*—The seed parent strain of *Mentha citrata* has deep red anthocyanin color development on stems, exposed stolons and leaf petioles and under some environmental conditions the leaves may be reddish or have a bronzed effect. In contrast, the Plot 4 strain has almost green stems with some anthocyanin development on the younger stems and the exposed stolons. To a casual observer, the Plot 4 strain may appear to be a green-stemmed and green plant. This anthocyanin pigmentation develops only in those parts of the plant exposed to sunlight.

*Plant pubescence.*—The seed parent and the Plot 4 hybrid are alike in appearing glabrous to the unassisted eye, but at 20× magnification both have a few short stubby hairs, especially on the leaf petioles and veins of the lower leaf surface, with a few stubby hairs found sparsely on the bracts to the flower spikes. Plot 4 generally has fewer hairs than the seed parent or the Plot 13 hybrid but this difference is not very definite and not very useful in distinguishing these strains.

*Calyx pubescence.*—The acuminate calyx lobes of the flowers of the Plot 4 strain are similar to those of the male parent in having ½–1 mm. long, white, unbranched calyx hairs which protrude from the calyx lobes. The seed parent strain of *Mentha citrata* has a few ¼–½ mm. long hairs on the lobes and veins of the calyx, but these hairs are less conspicuous than those found on the Plot 4 flowers. Similar hairs are found on the bracts in the flower spikes. There is considerable variation in the development of plant pubescence dependent upon maturity and the conditions under which the plants are grown.

*Corolla pubescene.*—The seed parent, the male parent and the Plot 13 hybrid strain are alike in having a few inconspicuous hairs on the outer lip of the corolla, but the Plot 4 strain does not have these hairs on the outer lip of the corolla.

*Flower pedicels.*—The seed parent, the male parent, the Plot 13 hybrid and the Plot 4 strain are essentially alike in having 1–2 mm. long flower pedicels. The flower pedicels of the male parent are hairy, whereas those of the seed parent are glabrous. The Plot 4 hybrid and the Plot 13 hybrid are alike in being essentially glabrous with a few very short hairs.

*Size differences of flower parts.*—No consistent essential differences were noted in the size of the flower parts despite the differences in chromosome numbers and origin.

*Number of flowers in a flower cluster.*—The seed parent and the Plot 4 hybrid usually have 15 flowers in each flower cluster, whereas the male parent frequently has 1–5 of the 15 flowers in the flower cluster aborted in fruiting specimens.

*Resistance to Verticillium wilt.*—The seed parent, as well as all other natural strains of *Mentha citrata* so far tested in our laboratory, are extremely susceptible to the pathogen *Verticillium albo-atrum* R. and B. var. *menthae* Nelson, whereas the male parent and the Plot 13 strain hybrid are very resistant to the pathogen in our 1966 wilt test on very welt-infested, organic soil of northern Indiana. This test plot was so thoroughly infested with wilt spores that peppermint, *Mentha piperita* L., and other susceptible mints were 90–100% infected and wilted. The Plot 4 strain hybrid has only slight wilt resistance, whereas the Plot 13 hybrid was the most resistant hybrid found in our 1966 wilt test.

*Resistance to various unidentified leaf spot diseases.*—While the male parent is very susceptible to certain leaf spot diseases, the Plot 4 hybrid, like the seed parent, is very resistant to these leaf spot diseases.

*Fertility.*—The seed parent is male sterile with rudimentary anthers but is seed fertile, whereas the Plot 4 strain is usually male sterile with rudimentary anthers and highly seed sterile when pollinated by other fertile species. In contrast, the male parent is wholly fertile.

*Diploid chromosome number.*—*Mentha citrata* Ehrh. has been reported as having 96 chromosomes. *Mentha crispa* L. from which the male parent was derived has been reported as having 48–51 chromosomes. The Plot 4 hybrid strain presumably has about 72 chromosomes since it was derived from crossing the above two fertile species.

Comparison of the male parent to the Plot 4 hybrid strain

From an overall viewpoint, the male parent (59–198) closely resembles *Mentha crispa* L. (also known as *Mentha spicata* L. var. *crispata*) from which it was derived, whereas the Plot 4 hybrid resembles the first generation hybrids obtained from hybridizing *M. citrata* Ehrh. or *Mentha aquatica* L. to *M. Spicata* L. or *M. crispa* L. Since the fertile species *M. aquatica* L. and *M. citrata* Ehrh. are reported as having 96 chromosomes and the fertile species *M. spicata* L. and *M. crispa* L. as having 48–51 chromosomes, one may presume logically that the $F_1$ hybrids have about 72 chromosomes. Under proper environmental conditions, the male parent is perfectly fertile, whereas the Plot 4 strain is usually male sterile like the seed parent but unlike the seed parent (which is seed fertile) is highly seed sterile.

The male parent (59–198) is an early maturing (almost all flowers gone on September 1st and bearing ripe seed in mid-September), short (11–13″ tall) with an erect, very much branched habit and fine, very wiry, stiff, slender stems whose diameter is 2–2.5 mm., whereas the Plot 4 hybrid is late maturing (in full bloom on September 1st), tall plant (17–26″ tall) with an erect, open, spreading, bush type habit and coarse stems whose diameter is 2.75–3.5 mm. The male parent has small (1–1½″ long x ⅝–⅞″ wide), ovate, very crisp leaves which are nearly sessile with very short petioles not exceeding 2 mm. and whose leaf margins are exceedingly lacerate with 3–5 mm. long fimbria, or finger-like teeth, that usually twist, whereas comparable mainstem leaves of the Plot 4 hybrid are large (1½–2⅝″ long x 1–1¼″ wide), ovate, flat, not crisp with 8–13 mm. long petioles and with the leaf margins bearing regular, serrate, conspicuous teeth that are not fimbria-like. Of less importance as distinguishing characteristics, the main axis very large, flat leaves of the Plot 4 strain usually have acute leaf apexes (sometimes rounded or obtuse on lowest leaves or in greenhouse plants, acute leaf bases, and do not twist nor bulge upward between major leaf veins, whereas the very crisp, lacerate leaves of the male parent are frequently very nearly as broad as long, twist and curl, usually have acute leaf apexes, cordate leaf bases and bulge upward between the major leaf veins.

The male parent has a menthone-pulegone odor, since menthone and pulegone are the principal oil components in this strain, whereas there are only trace amounts (if any) of linalyl acetate and linalool, the principal oil components of the Plot 4 hybrid strain.

The 20–40 mm. long flower spikes of the male parent are narrowly cylindrical (6–7 mm. in diameter in fruiting specimens) and resemble the flower spikes of *Mentha crispa,* whereas the 30–50 mm. long flowering spikes of the Plot 4 strain are more broadly cylindrical (10–14 mm. in diameter in fruiting specimens) and more nearly resemble the flowering spikes of peppermint, *M. piperita* L.

Of much less interest as a distinguishing characteristic, the male parent and the Plot 4 hybrid are alike in appearing essentially glabrous to the unassisted eye but at 20× magnification do have a few long hairs on the stems, bracts to the flower clusters and the lower leaf surface (especially the midrib), but the male parent has a few inconspicuous hairs on the outer lip of the corolla, whereas the Plot 4 hybrid does not.

The male parent strain 59–198 derived from fertile *Mentha crispa* is fully fertile and was used in this plant breeding program since it has excellent stolons which over winter well, and since it is very highly resistant to the pathogen, *Verticillium albo-atrum* R. and B. var. *menthae* Nelson, whereas the Plot 4 hybrid has only slight resistance to this pathogen. While the male parent is very susceptible to certain unidentified leaf spot diseases, the Plot 4 strain is very resistant to these same leaf spot diseases, having secured this resistance from the seed parent.

I claim:

1. A new and distinct variety of mint plant substantially as herein shown and described, being an adapted high-yielding strain characterized particularly by its production of an oil with a relatively high linalyl acetate content, when compared to the oil of its *Mentha citrata* seed parent, and at most only minor amounts of menthone and pulegone, which are the principal components of the oil of its male parent, said oil having a pleasant lavender odor with definite terpeneless bergamot characteristics; its excellent stolons which are winter hardy; and its hardy characteristics under climatic conditions favorable to the growth of mint plants as represented by *Mentha piperita* L., especially in the Oregon and Idaho areas of mint production.

No references cited.

ROBERT E. BAGWILL, Primary Examiner